(12) United States Patent
Sun

(10) Patent No.: US 7,300,627 B1
(45) Date of Patent: Nov. 27, 2007

(54) TEST SAMPLE COLLECTION SYSTEM

(75) Inventor: Ming Sun, Cherry Hill, NJ (US)

(73) Assignee: Sun Biomedical Laboratories, Inc., Blackwood, NJ (US)

( * ) Notice: Subject to any disclaimer, the term of this patent is extended or adjusted under 35 U.S.C. 154(b) by 761 days.

(21) Appl. No.: 10/192,464

(22) Filed: Jul. 10, 2002

(51) Int. Cl.
*G01N 33/00* (2006.01)

(52) U.S. Cl. ............... 422/58; 422/55; 422/56; 422/57; 422/100; 422/104

(58) Field of Classification Search ......... 422/50, 422/55, 58, 68.1, 82.05, 102, 104, 56, 57, 422/99, 100; 435/5, 6, 7.1, 7.2
See application file for complete search history.

(56) References Cited

U.S. PATENT DOCUMENTS

| | | | |
|---|---|---|---|
| 4,818,677 A * | 4/1989 | Hay-Kaufman et al. ...... 435/4 |
| 4,943,522 A * | 7/1990 | Eisinger et al. ........... 435/7.25 |
| 5,017,342 A | 5/1991 | Haberzetti et al. |
| 5,207,984 A * | 5/1993 | Kheiri ................... 422/58 |
| D342,575 S * | 12/1993 | Ashihara et al. ......... D24/224 |
| 5,384,264 A * | 1/1995 | Chen et al. .............. 436/525 |
| 5,962,336 A | 10/1999 | Sun |
| D421,310 S * | 2/2000 | Shantz ................... D24/223 |
| 6,046,058 A | 4/2000 | Sun |
| 6,303,081 B1 * | 10/2001 | Mink et al. ............... 422/61 |
| 6,372,514 B1 * | 4/2002 | Lee ........................ 436/518 |
| 6,372,516 B1 | 4/2002 | Sun |
| 6,375,896 B1 * | 4/2002 | Wuske et al. ............ 422/58 |

OTHER PUBLICATIONS

AVITAR, Inc., Oral Screen, 1999 Brochure

* cited by examiner

*Primary Examiner*—Jill Warden
*Assistant Examiner*—Samuel P Siefke
(74) *Attorney, Agent, or Firm*—Norman E. Lehrer

(57) ABSTRACT

A collection system for collecting a liquid test sample that includes a spoon-like member having a bowl portion for collecting and holding the test sample, a handle member housing a test device, and a channel member joining the bowl portion to the handle member is disclosed. The channel member provides an elongated passageway for transferring the test sample to the test device. A cap is releasably mounted on the channel member and covers the bowl portion and the channel member. The bowl portion and channel member are inclined slightly upwardly from the horizontal thereby allowing the test sample to flow from the bowl portion, through the channel member, and into the handle member. A cover is releasably mounted on the channel member and can be secured to the handle member.

8 Claims, 2 Drawing Sheets

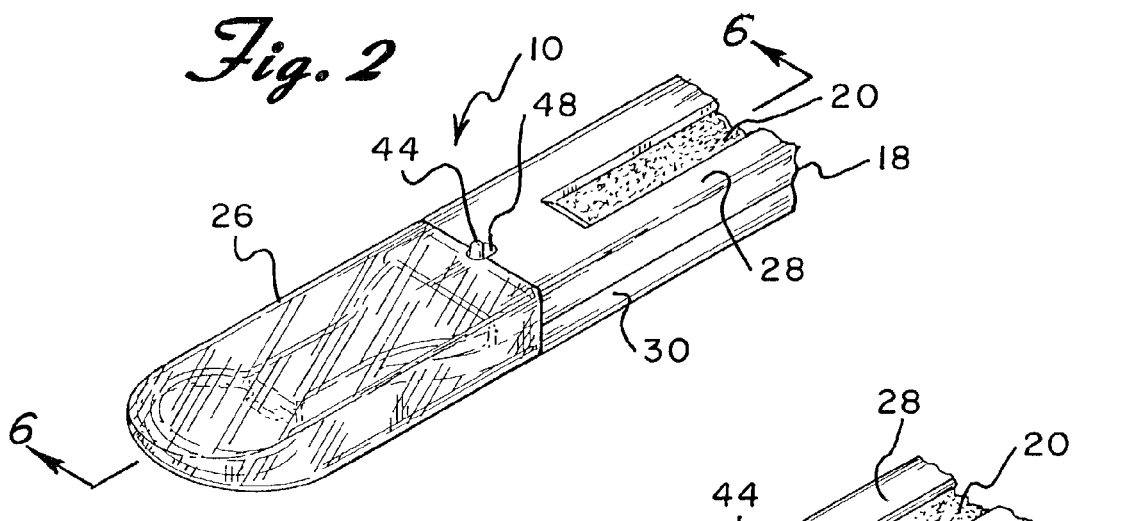
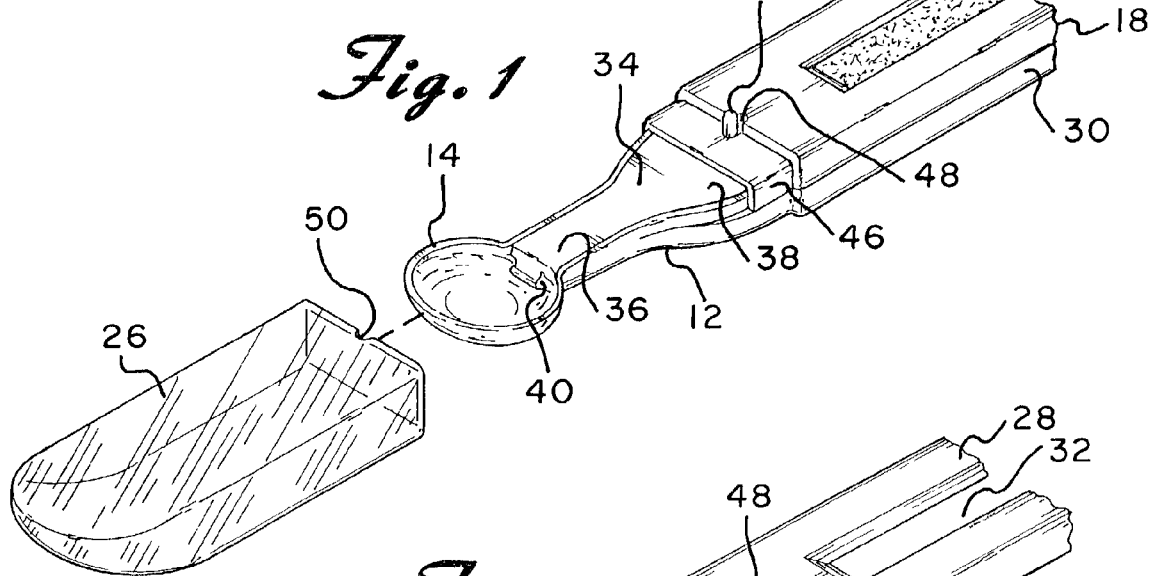
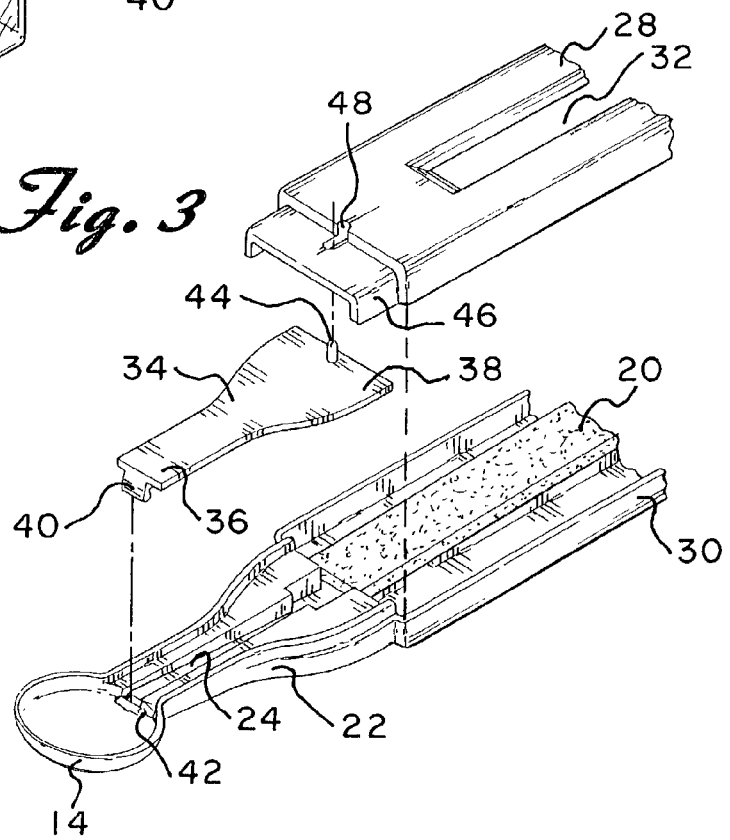

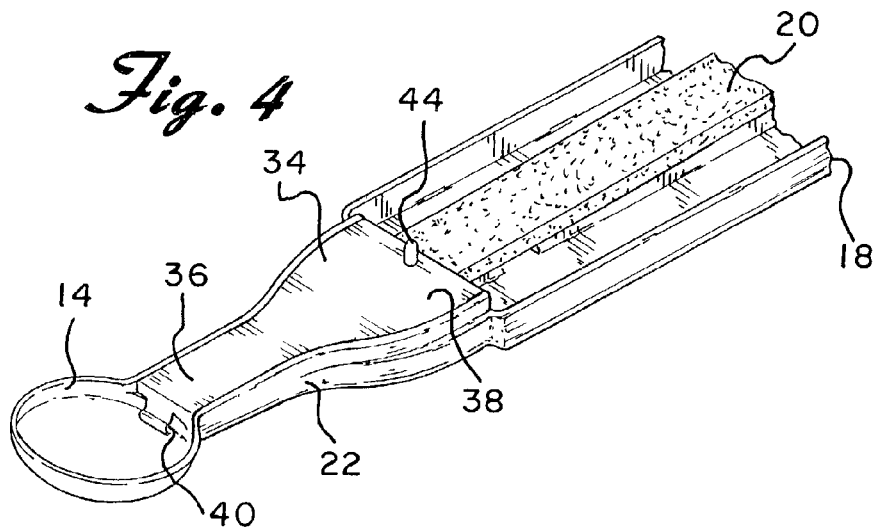
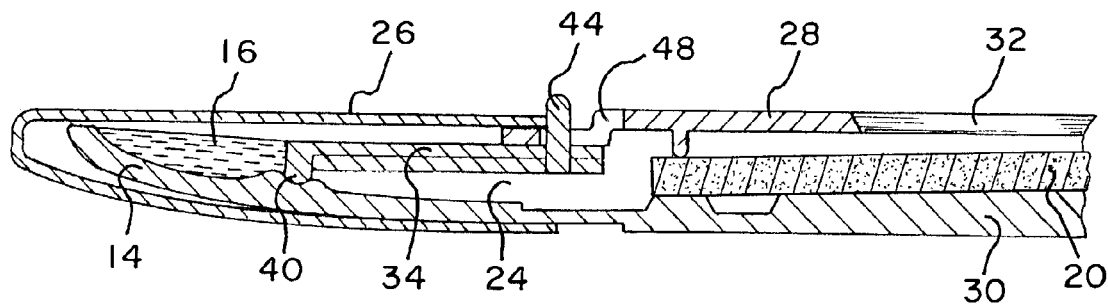
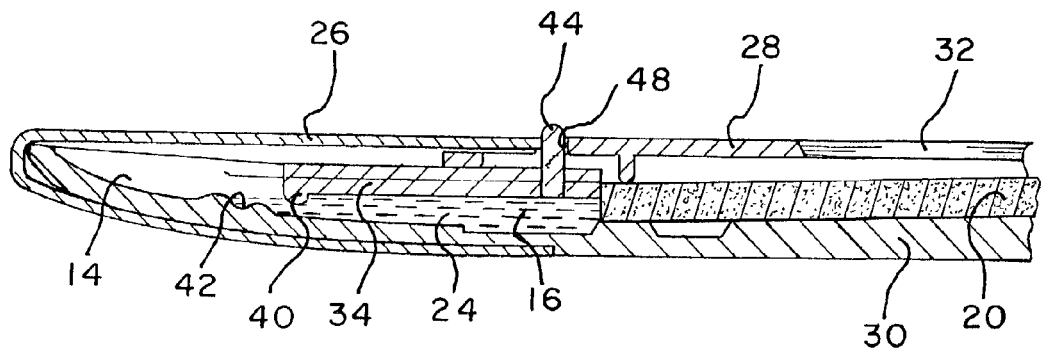

TEST SAMPLE COLLECTION SYSTEM

BACKGROUND OF THE INVENTION

The present invention is directed toward a test sample collection system and more particularly, toward a device that can be used to collect a sample in a quick and accurate manner.

There are many methods that allow for a test sample to be collected in order to analyze the sample. For example, Applicant's prior patent, U.S. Pat. No. 6,372,516 uses an absorbent pad to collect a sample where the pad comes into contact with a test strip from which a reaction, if any, can be seen. The present invention is an improvement over Applicant's prior invention which allows for quicker and more consistent results.

Another method for collecting fluid samples currently being used and available through Avitar includes a foam head attached to an elongated handle. Attached to the handle is a hood that is movable along the handle. The foam head is placed into a person's mouth so that fluid enters the foam. The hood is slid forward, over the foam head. The hood is squeezed so that fluid contained therein is expelled into a sample well for testing. This device, however, appears to require a great deal of manipulation and handling of the test device by the person taking the test and the person conducting the test.

Therefore, a need exists for a test sample collection device that is simple to use and provides accurate results in a quick and consistent manner.

SUMMARY OF THE INVENTION

The present invention is designed to overcome the deficiencies of the prior art discussed above. It is an object of the present invention to provide a collection device for a test sample which is simple to use and provides accurate, consistent results.

It is another object of the present invention to provide a collection device which may be used with different types of test strips.

In accordance with the illustrative embodiments demonstrating features and advantages of the present invention, there is provided a collection system for collecting a liquid test sample that includes a spoon-like member having a bowl portion for collecting and holding a liquid test sample, a handle member housing a test device, and a channel member joining the bowl portion to the handle member, the channel member provides an elongated passageway for transferring the test sample to the test device, and a cap releasably mounted on the channel member and covering the bowl portion and the channel member. The bowl portion and channel member are inclined slightly upwardly from the horizontal thereby allowing the test sample to flow from the bowl portion, through the channel member, and into the handle member. The handle member includes a housing with a top half and a bottom half within which the test device is located. A cover is releasably mounted on the channel member and can be secured to the handle member.

Other objects, features, and advantages of the invention will be readily apparent from the following detailed description of a preferred embodiment thereof taken in conjunction with the drawings.

BRIEF DESCRIPTION OF THE DRAWINGS

For the purpose of illustrating the invention, there is shown in the accompanying drawings one form which is presently preferred; it being understood that the invention is not intended to be limited to the precise arrangements and instrumentalities shown.

FIG. 1 is a top perspective view of the collection device of the present invention with the cap removed;

FIG. 2 is a top perspective view of the collection device of the present invention with the cap in place;

FIG. 3 is an exploded view of the collection device of the present invention;

FIG. 4 is a top perspective view of the present invention with portions removed for clarity;

FIG. 5 is a cross-sectional view of the present invention before the cap is in its fully locked position; and FIG. 6 is a cross-sectional view taken through line 6-6 of FIG. 2.

DETAILED DESCRIPTION OF THE PREFERRED EMBODIMENT

Referring now to the drawings in detail wherein like reference numerals have been used throughout the various figures to designate like elements, there is shown in FIG. 2 a test sample collection system constructed in accordance with the principles of the present invention and designated generally as 10.

The test sample collection device essentially includes a spoon-like member 12 having a bowl portion 14 for collecting and holding a liquid test sample 16, a handle member or stem 18 housing a test device 20, and a channel member 22 providing means 24 for transferring the test sample 16 to the test device 20 and a cap 26 releasably mounted on the channel member 22 and covering the bowl portion 14 and the channel member 22. The bowl portion 14 may be round, oval, or similarly shaped. The bowl portion may hold from approximately 100-600 microliters of a sample. The size of the bowl portion may be made smaller, that is, in order to collect less sample by placing an adapter or filter member therein. The device may be made from polyethylene or similar material.

The handle member 18 includes a top half 28 and a bottom half 30 with the test device 20 located therebetween. The top and bottom halves 28 and 30 fit together in a manner typically known in the art, thereby forming a housing. For example, pins may be located along the inside perimeter of the top half of the housing where each pin fits in a respective hole formed along the periphery of the interior of the bottom half of the housing.

Preferably, the end of the test device 20 and the interior surface at the corresponding end of the bottom half 30 of the housing are inclined slightly upwardly from the horizontal, for example, at an angle of approximately in the range of five to thirty degrees in order to prevent the liquid test sample from flowing passed the test strip. (See FIGS. 5 and 6.) This helps to concentrate the liquid in the test reaction area. The test device 20 may otherwise fit within the bottom half 30 of the housing in a manner similar to that described in Applicant's prior U.S. Pat. Nos. 6,372,516; 6,046,058; and 5,962,336. A window 32 may be located in the top half 28 of the housing so that the test reaction may be seen therethrough. The window may include a concave plastic cover so that the test results are amplified.

The test device may be an immunoassay test strip of the type described in Applicant's U.S. Pat. No. 6,372,516.

However, almost any type of test strip may be used. The test strip may be used to analyze any type of substance as well. For example, the test device may be used to test for the presence of particular drugs in saliva, urine, or other body fluids.

The transferring means 24 of the channel member 22 includes an elongated passageway connecting the bowl portion 14 with the housing of the handle member. The passageway 24 acts as a conduit for the test sample 16. That is, the test sample 16 flows from the bowl portion 14 to the test device 20. A cover 34 is releasably mounted to the channel member 22. The cover 34 is complimentary in shape to the channel member 22 and has an elongated front portion 36 and an expanded rear portion 38. The cover 34 may be transparent so that the flow of the sample 16 can be monitored. Located adjacent the front portion 36 is a means for temporarily preventing the test sample 16 from flowing through the channel member 22. The preventing means may include a gate in the form of a downwardly extending flange 40. A notch 42 is formed within the bowl portion 14 and is located directly below the flange 40 so that the flange 40 fits therein to form a dam. (See FIG. 4.) The function of the flange will be described in greater detail below.

Located adjacent the rear portion 38 of the cover 34 is an upwardly extending protrusion or pin 44. The protrusion 44 extends from the outer surface of the cover 34. The handle member 18 has an extension 46 formed adjacent the front of the top half 28 of the housing. An elongated aperture 48 is formed in the extension 46 and in the top half 28 of the housing. (See FIG. 3.) The protrusion 44 fits through the aperture 48, thereby securing the channel member 22 to the handle member 18.

The bowl portion 14 and channel member 22 are inclined slightly upwardly from the horizontal, thereby allowing the test sample 16 to flow from the bowl portion 14, through the channel member 22, and into the housing of the handle member 18 where the test device 20 is located. (See FIGS. 5 and 6.)

The cap 26 fits over the bowl portion 14 and channel member 22 and has a cut-out portion 50 which is aligned with the aperture 48 formed in the top half 28 of the housing. (See FIG. 2.) The function of the cap will be described in greater detail below.

In order to use the device of the present invention, the cap 26 is removed from the device. (See FIG. 1.) The bowl portion 14 is used to collect the test sample 16. This may involve placing the bowl portion into a person's mouth so that saliva gathers therein or by dipping the bowl portion into the source. The cap 26 is then replaced onto the device so that the cap 26 contacts the protrusion 44 of the housing. (See FIG. 5.) Pushing the cap 26 to further engage the protrusion 44, the protrusion 44 is pushed back within the aperture 48 which causes the flange 40 to move upwardly. This action, along with the incline of the bowl portion 14 and the channel member 22, allows the sample 16 to flow through the passageway 24 and into contact with the test device 20 located within the housing. (See FIG. 6.) The sample flows through the device and to the test device in a quick and controlled manner without over or under saturation of the test strip. The sample reaches the reaction zone of the test device via capillary action. Any reaction may be viewed through the window.

The present invention may be embodied in other specific forms without departing from the spirit or essential attributes thereof and accordingly, reference should be made to the appended claims rather than to the foregoing specification as indicating the scope of the invention.

I claim:

1. A collection system for collecting a liquid test sample comprising:
    a spoon-like member having a bowl portion for collecting and holding a liquid test sample, a handle member housing a test device, and a channel member joining said bowl portion to said handle member, said channel member providing means for transferring the test sample to the test device and said channel member including a cover releasably mounted on said channel member;
    means for temporarily preventing the test sample from being transferred to the test device, said preventing means including a flange extending downwardly from said cover and a notch formed within said bowl portion within which said flange fits; and
    means for securing said cover to said handle member
    wherein said handle member includes a housing with a top half and a bottom half with the test device located between said top half and said bottom half and wherein said securing means includes an aperture formed in said top half of said housing and an upwardly extending protrusion formed on said cover of said channel member, said protrusion extending through said aperture.

2. The collection system for collecting a liquid test sample of claim 1 further including a cap for covering said bowl portion and said channel member and wherein said cap has a cut-out portion capable of being aligned with said aperture of said housing.

3. The collection system for collecting a liquid test sample of claim 1 wherein said bowl portion and said channel member are inclined slightly upwardly from the horizontal thereby allowing the test sample to flow from said bowl portion, through said channel member, and into said housing.

4. The collection system for collecting a liquid test sample of claim 2 wherein said cap is capable of moving said protrusion out of said aperture which causes said flange to move upwardly so that the test sample may flow into said housing.

5. The collection system for collecting a liquid test sample of claim 1 further including a cap releasably mounted on said channel member and covering said bowl portion and said channel member.

6. The collection system for collecting a liquid test sample of claim 1 wherein said transferring means includes an elongated passageway through which the test sample may flow.

7. The collection system for collecting a liquid test sample of claim 1 wherein said test device is inclined slightly upwardly from the horizontal at an angle in the range of approximately five to thirty degrees.

8. The collection system for collecting a liquid test sample of claim 1 wherein said bowl portion is adapted to hold a volume within the range of approximately 100-600 microliters of the test sample.

* * * * *